US012716091B2

(12) United States Patent
Bhakdi

(10) Patent No.: US 12,716,091 B2
(45) Date of Patent: Aug. 25, 2026

(54) HYBRID MANUAL-MACHINE LEARNING PCR CURVE ANALYSIS AND CLASSIFICATION

(71) Applicant: QuantGene Inc., Santa Monica, CA (US)

(72) Inventor: Johannes Bhakdi, Los Angeles, CA (US)

(73) Assignee: QuantGene Inc., Santa Monica, CA (US)

( * ) Notice: Subject to any disclaimer, the term of this patent is extended or adjusted under 35 U.S.C. 154(b) by 1184 days.

(21) Appl. No.: 17/702,573

(22) Filed: Mar. 23, 2022

(65) Prior Publication Data

US 2022/0307069 A1 Sep. 29, 2022

Related U.S. Application Data

(60) Provisional application No. 63/165,076, filed on Mar. 23, 2021.

(51) Int. Cl.

| | |
|---|---|
| ***C12Q 1/686*** | (2018.01) |
| ***G06N 5/02*** | (2023.01) |
| ***G06N 5/022*** | (2023.01) |
| ***G16B 40/30*** | (2019.01) |

(52) U.S. Cl.

CPC ............. *C12Q 1/686* (2013.01); *G06N 5/022* (2013.01); *G16B 40/30* (2019.02)

(58) Field of Classification Search

CPC ................................ C12Q 1/686; G06N 20/00

See application file for complete search history.

(56) References Cited

U.S. PATENT DOCUMENTS

| | | | | |
|---|---|---|---|---|
| 2010/0184067 A1* | 7/2010 | Abe | ..................... | C12Q 1/6851 435/6.1 |
| 2017/0247745 A1* | 8/2017 | Shultz | ................ | G01N 21/6428 |
| 2021/0147924 A1* | 5/2021 | Galvin | ................... | G16B 30/00 |

(Continued)

FOREIGN PATENT DOCUMENTS

| | | | |
|---|---|---|---|
| EP | 1335028 A2 * | 8/2003 | .......... C12Q 1/6851 |
| EP | 2780853 B1 * | 5/2019 | ............ G16B 45/00 |

OTHER PUBLICATIONS

MacLean et al., "Automation and standardisation of clinical molecular testing using PCR.Ai—A comparative performance study", Nov. 2019, Journal of Clinical Virology, vol. 120, pp. 51-56. (Year: 2019).*

(Continued)

*Primary Examiner* — Paulinho E Smith
(74) *Attorney, Agent, or Firm* — Cognition IP, P.C.; Edward Steakley; Schiller Hill

(57) ABSTRACT

Methods, systems and apparatus for the analysis of biological samples. Biological sample held in sample plates may be processed by a PCR machine. PCR curves are generated for each biological sample and analyzed by one or more machine learning models. The PCR curves are assigned a confidence level and classified based on the analysis and the confidence level. PCR curve with a confidence level below a predetermined threshold may be flagged for analysis by a lab director. PCR curves flagged for manual analysis may be displayed on an analysis interface. The lab director may view, analyze and classify the flagged PCR curves through interaction with the analysis interface.

20 Claims, 12 Drawing Sheets

(56) References Cited

U.S. PATENT DOCUMENTS

| | | | | |
|---|---|---|---|---|
| 2021/0214768 | A1* | 7/2021 | Sinha | C12Q 1/6806 |
| 2021/0238667 | A1* | 8/2021 | Georgiou | C12Q 1/6858 |
| 2022/0119876 | A1* | 4/2022 | Salk | C12N 15/1065 |
| 2022/0307069 | A1* | 9/2022 | Bhakdi | C12Q 1/686 |
| 2023/0022761 | A1* | 1/2023 | Filippis | G16H 50/00 |
| 2023/0326553 | A1* | 10/2023 | Rodriguez Manzano | G16B 40/10 706/20 |
| 2024/0124945 | A1* | 4/2024 | Del Vecchio | G01N 35/1095 |

OTHER PUBLICATIONS

Moniri et al., “Amplification Curve Analysis: Data-Driven Multiplexing Using RealTime Digital PCR”, 2020, Analytical Chemistry, vol. 92, pp. 13134-13143. (Year: 2020).*

Athamanolap et al., “Integrated Bacterial Identification and Antimicrobial Susceptibility Testing Using PCR and High-Resolution Melt”, 2017, Analytical Chemistry, vol. 89, pp. 11529-11536. (Year: 2017).*

* cited by examiner

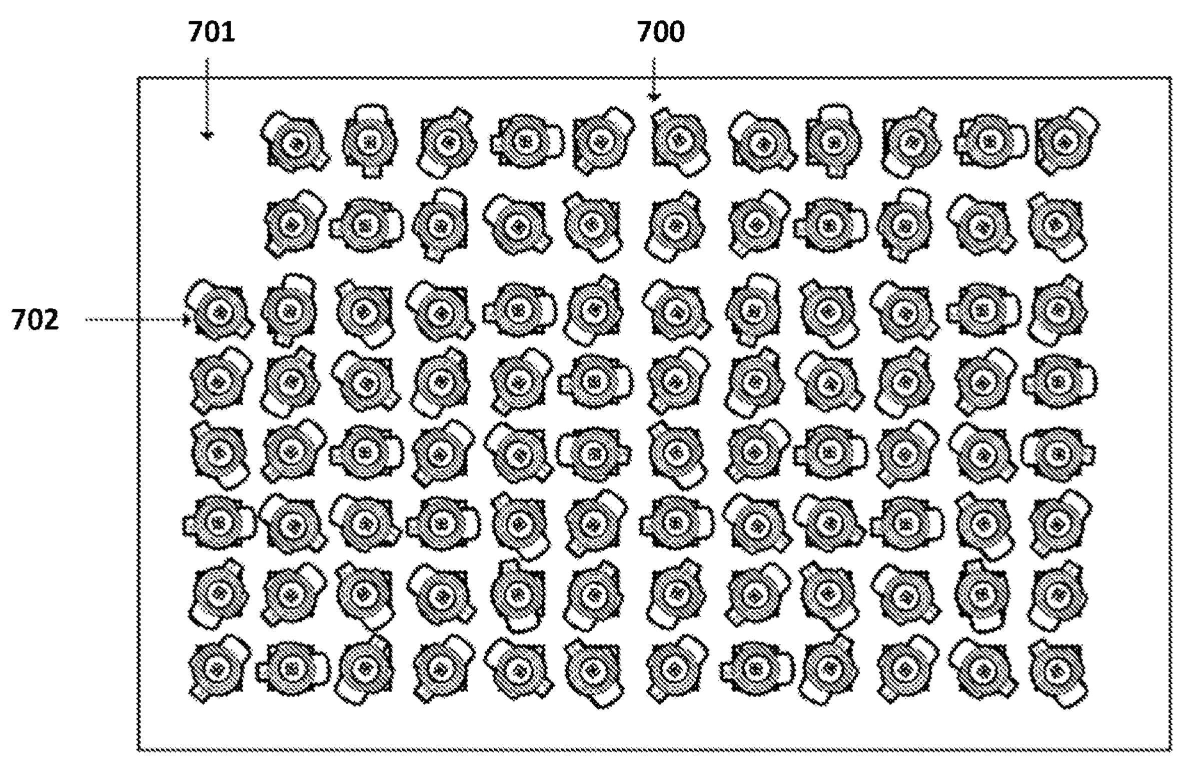
FIG. 7A
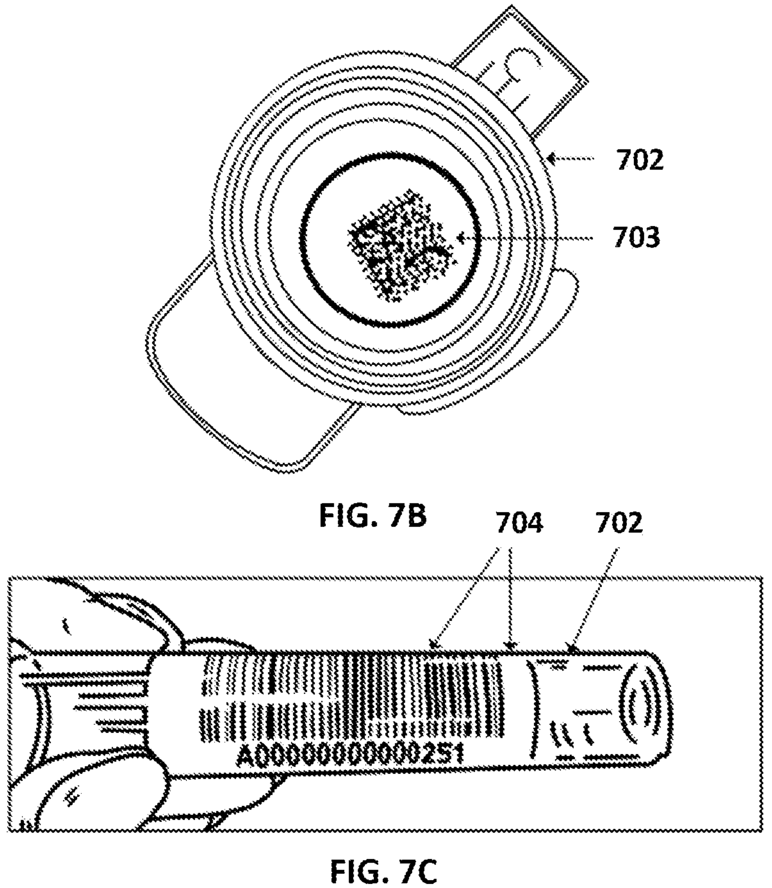
FIG. 7B
FIG. 7C

HYBRID MANUAL-MACHINE LEARNING PCR CURVE ANALYSIS AND CLASSIFICATION

CROSS-REFERENCE TO RELATED APPLICATIONS

This application claims the benefit of U.S. Application No. 63/165,076 filed on Mar. 23, 2021, which is incorporated herein by reference in its entirety.

FIELD

The present invention relates generally to the managing, tracking and analysis of biological samples, the use of computer vision to recognize the containers that hold the samples to visually register and verify the possession of the samples and the analysis of biological samples through the use of machine learning models.

BACKGROUND

In a traditional approach to collection and testing of biological samples from patients at a provider facility, a nurse or technician would collect a sample from the patient and mail or transfer that sample to a laboratory for processing. At the laboratory, the samples are received and must be entered into the laboratory system. The labels may have different labeling on them when they come from different providers. The lack of organizing of the received samples leads to a slow process that is prone to error. For example, a laboratories that processes 15,000 biological samples a day will need to employ 150 full time employees to perform sample accessioning.

The process of receiving the samples, entering the samples into the system and accessioning/transferring the samples is not even fully digital. In most cases a lab technician would need to scan all of the received tubes holding the samples to enter them into the system. In some cases the lab technician would enter the received samples into the system manually through a keyboard or other input method. The lab technician would then create a list of the sample tubes received and print the list. At this point the lab technician or sample accessioning technician would take the sheet and use it to document the transference of samples from the tubes to wells in a sample plate. The technician would mark the well number next to the tube entry on the printed list/sheet. The technician may also need to write labels on the tube to indicate the position of the sample in the sample plate., next to the tube well number in which then writes, next to each tube, the well number.

After the technician has transferred all the samples into the sample plate and documented the locations of the samples, the technician then needs to enter that information into the system. This entry is usually performed manually and may be prone to errors. The errors may arise from the initial entry of the samples into the system upon reception, transference of samples from unorganized sample tubes, the documenting of the well number for the samples, the entering of the documented well numbers for the samples or a number of other human errors.

Analysis of the diagnostic results are then performed by a lab director at the facility processing the biological samples. This flow results in a slow and inefficient process with little procedural transparency.

SUMMARY

The systems and methods described herein provide for the tracking and managing of biological samples. In one embodiment, a one or more providers may collect a biological samples from one or more patients at a provider facility. The provider may use a provider device, connected to a provider terminal, either wired or wirelessly. A dashboard, terminal or portal may be displayed to the provider through a display connected to the provider terminal or the provider device.

The provider device and provider terminal may be in communication with one or more databases, one or more application servers and one or more analysis servers. In some embodiments, the provider may collect a biological samples from a patient. The collected biological sample may then be placed into a test tube. The test tube may have one or more labels or visual indicators affixed. For example, a QR code may be affixed to the top or lid of the test tube and a barcode may be affixed to the side of the test tube.

The labeled test tubes may be aggregated into one or more racks, wherein the one or more racks are arranged in a grid pattern with coordinates for the rows and columns. The rack may also have a have a QR code, visual marker, fiducial marker, landmark or other physical or visual indicator of the orientation of the rack.

In some embodiments, a provider may capture one or more images with a provider device. Provider devices may include smartphones, tablets, laptops or other devices with one or more camera sensors configured to capture images of the rack. The one or more images of each rack may be analyzed to identify the orientation of the rack within the captured images, identify one or more test tubes held by the rack, read a QR code for each identified test tube and associate each test tube with a patient based on the read QR code. The association and registration of the patient with their sample, the sample with the test tube and the test tube with the rack may be tracked and monitored by the system and stored in the provider terminal, an application server, an analysis server and/or a database. Information related to the one or more racks, the test tubes held by each rack and the patients associated with each test tube may also be stored.

In some embodiments, a status of each rack and each sample may be maintained in a central location, and accessible by the patient, the provider or the lab. The status of the racks and test tubes may be updated in real-time at each step in the process. Every action and interaction with a rack or sample may generate an update to the status and the information associated with the rack or sample.

The dashboard, terminal or portal may display information related to the rack and samples in real-time as they are updated. Push notifications may be generated to alert providers, lab workers and patients of any changes in the processing of their sample, including location of their sample, progress of their sample in the testing process and results of the testing performed on the sample.

In some embodiments, the provider facility may initiate a transfer of the racks to a destination lab for processing. Upon receipt of the racks, a lab device may be used to capture images of each rack. The images may then be analyzed to identify the racks, read QR codes from the test tubes, retrieve patient information associated with each test tube and verify/validate the received racks/sample. The analysis may be used to guarantee that all samples are accounted for, maintaining a clear chain of custody and an auditable trail.

In some embodiments, after analyzing and validating the received racks and samples, each rack may then be associated with a corresponding sample plate. Each biological sample from a rack may then be transferred to the sample plate associated with it. The biological samples may be transferred from each test tube to a plate well of the sample plate. The plate well position of transferred biological sample directly corresponds to the rack position of the test tube that the sample was transferred from.

The sample plate may be transferred or loaded into a PCR system. A PCR test procedure may then be initiated for each sample plate of the sample plate. Upon performing the PCR testing procedure on each biological sample, an analysis may be performed on the results of the PCR test procedure. The analysis may be performed by one or more machine learning models operating on an analysis server, lab device, application server, lab terminal or any system with memory for storing the machine learning model, information related to the PCR test for each sample and a processing unit to execute the one or more machine learning models.

In some embodiments, the one or more machine learning models may assign a confidence level to each result. Results with a confidence level at or above a predetermined threshold level may be considered accurate. Each accurate result may be associated/linked/added to a patients record and stored in the database, application server and/or analysis server to. The results may also be stored without the association with a patient in an anonymized manner to protect the identity of the patient. A hash or distributed ledger may be used to store personal information of the patient and the results of the testing. Distributed ledgers such as block chain may be used in the implementation. Public-private key encryption may also be used in the authorization verification when accessing stored patient records, provider records or lab records.

In some embodiments, the patient records may be hashed. At each update, the updated information may be added to the hashed record and hashed again. This may be used to maintain a secure audit trail that cannot be modified. Both public and private keys may be used in the hashing.

In some embodiments, a qualified user may be alerted for each result with a confidence level below a predetermined threshold. Qualified users may be users qualified to analyze PCR test results, such as a lab director, lab specialist or a user with sufficient training to allow them to perform the analysis. Upon receiving the alert, the qualified user may perform an analysis on the PCR test results. The determination made by the qualified user may then be stored as is disclosed above.

BRIEF DESCRIPTION OF THE DRAWINGS

The present disclosure will become better understood from the detailed description and the drawings, wherein:

FIG. 7A is a diagram illustrating an exemplary tube rack in accordance with aspects of the present disclosure.

FIG. 7B is a diagram illustrating an exemplary sample tube in accordance with aspects of the present disclosure.

FIG. 7C is a diagram illustrating an exemplary sample tube in accordance with aspects of the present disclosure.

DETAILED DESCRIPTION

Figure 1:
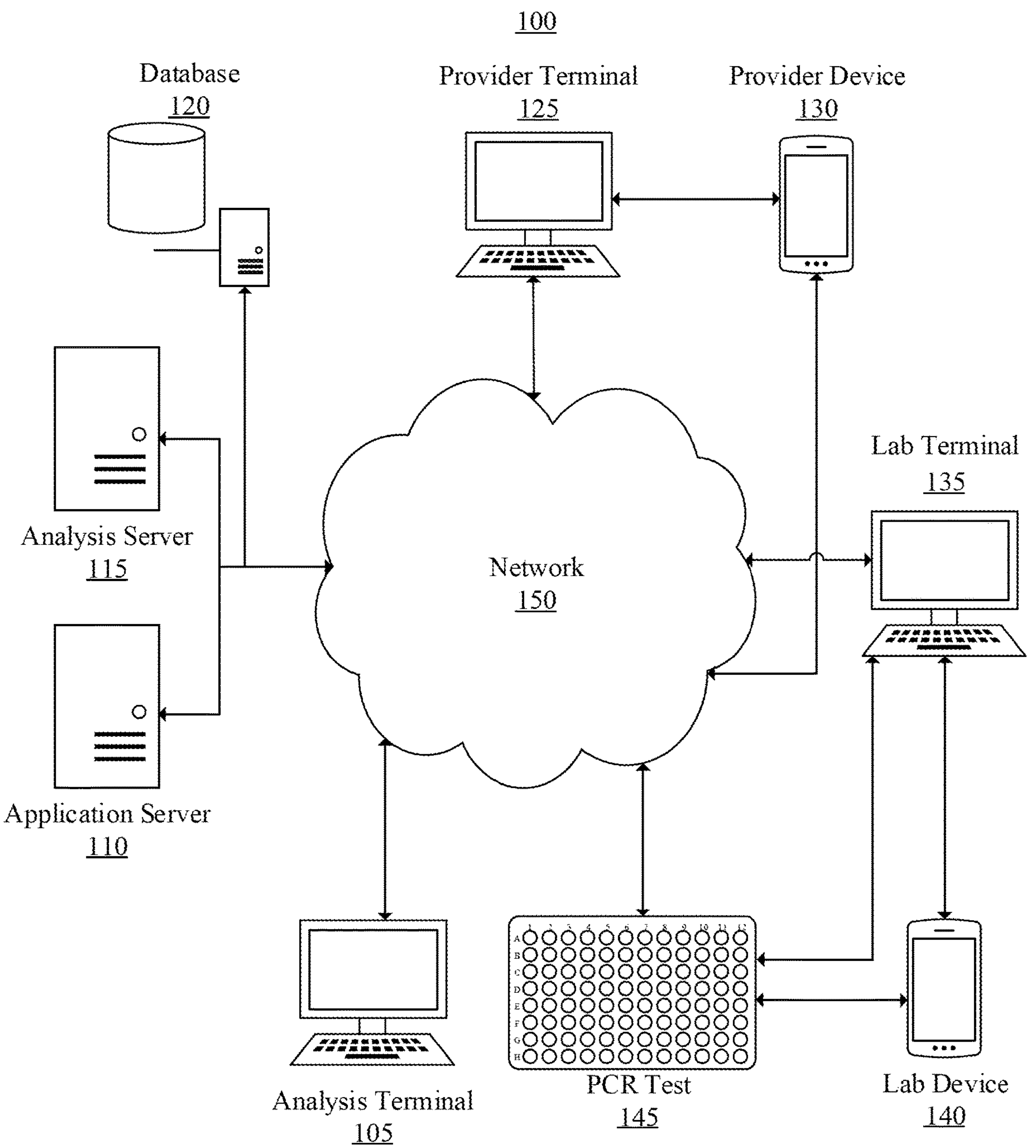
FIG. 1 is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

The following generally relates to a system and methods for managing and tracking biological samples from a provider facility to a testing facility (destination lab). In some embodiments, a database, application server, analysis server, lab terminal and provider terminal may be configured to operate cooperatively as a cloud based system. All patient data may be stored on the cloud, either in the database, application server, analysis server, lab terminal or provider terminal.

In some embodiments, a patient may enter a provider facility to have a biological sample taken and tested. A provider/nurse may receive the patient and check the patient into the system. If the patient is not already registered into the system, the nurse may then create a new patient record for the patient. The checking in of the patient and registering of a new patient may be performed on a provider terminal or a provider device, such as a tablet computer or smartphone. After the check-in or registration of a new user, the nurse may select the patient in the system and scan a barcode or QR code on a test tube to associate the test tube to the patient. At this point, the same or different nurse may use the test tube to collect a biological sample from the patient. The registration and collection may be performed in the same location, such as in a room designated for the collection of biological samples or in a drive-through setting, where the registration, scanning and sample collection may be performed on a patient while they remain in their vehicle (i.e. SARS-CoV-2 drive-through/drive-up testing). Alternatively, the patient may be given the tube and instructed to proceed to another location with the tube to have the biological sample collected.

In some embodiments, upon collection of a biological sample from a patient, the nurse may place the tube containing the sample into a rack. The aggregation of the samples into one or more racks provides a central organized storage for all collected samples, reducing the possibility of losing samples and errors.

The rack allows for the storage and transportation of sample tubes. Sample tubes may be loaded in any order or rearranged. Sample tubes may be replaced/exchanged with sample tubes from other racks. Additional sample tubes may be added to racks that are not full. The changing, exchanging, adding, replacing and removing of sample tubes may all be performed without losing any of the information associated with the sample tubes.

For example, there may be many racks that are only partially filled. The sample tubes may be aggregated so as to use the least number of racks possible. The sample tubes may be moved from one or more partially full racks to another partially full rack until all racks are full or all but one is full, with the partially full rack being organized with sample tubes occupying positions starting from the top left of the rack (increases downward and to the right).

Images of the racks may be captured and analyzed to identify the tubes held in the rack. Racks may be full or partially full. The identified tubes may be associated with the rack and tracked throughout the testing process. If any changed are made to the rack, such as tubes being removed, added or exchanged, the racks that have been affected would need to be imaged and analyzed again, and the record for the rack and tube would need to be updated on the system. This is much faster and efficient and less error prone that the traditional method of adding or removing samples from a batch of samples to be analyzed. Traditionally, a provider would need to find the tube in a batch of tubes, remove the tube, find the record of the tube in the system and remove it from the batch. In an unorganized collection of tubes, it may be hard to find the tube that is to be removed. When a tube needs to be removed from the disclosed invention, the provider may be given the rack location and the position of the tube within the rack. This allows for the provider to instantly know where the tube is. In this example, when a tube is removed from a position that is not the last occupied position of the rack, the tube in the last position of the rack or a new tube may be placed in the empty, previously occupied position.

At the provider location, a nurse or other provider employee may capture images of the racks, package the racks in compliance with a transportation method to be used to transfer the racks to a destination facility and initiate the transfer (i.e. mail, courier, walking, intern) of the racks to the destination facility.

At the destination lab, a lab tech may receive the one or more racks from one or more provider facilities as well as individual samples mailed from patients. The destination lab may receive samples in a mixed format (i.e. some bagged and some in racks). Upon receipt, the lab tech may capture images of the one or more racks, in a similar manner to that described above. The analysis of the images may be used to verify that all the samples were received as well as retrieve patient information and update the status of the racks and samples.

In some embodiments, the racks may be processed (i.e. image analysis/scanning and sample transfer) as they are, even if the racks are only partially full. In some embodiment, the racks may be scanned as they are, even if the racks are only partially full, for verification purposes, but additional tubes may be added to fill up the empty spaces before sample transfer to a sample plate. In this embodiment, after verification of the partially full rack additional sample tubes may be placed into empty slots of the rack and scanned into the system to register the additional sample tubes with the current rack/batch of samples being tested. This would minimize the number of racks needed to hold the sample tubes, the number of sample plates to transfer the samples to and the number of testing runs (PCR).

In some embodiments, racks that are partially full may have additional sample tubes placed in the open spaces in order to fill as much of the rack as possible. The additional sample tubes may be samples received in the mail directly from patients, from bagged sample tubes, sample tubes of samples that need to be rerun or sample tubes from other racks. After filling a rack with additional sample tubes, the rack may then be processed. Scanning of the full rack with a mix of original sample tubes and new sample tubes may be used for verification of sample receipt. Upon scanning, the samples tubes may be checked against a manifest to guarantee that all samples are accounted for. This manifest may be stored on the database and verified and updated at each step of the process. This manifest may use a distributed ledger to maintain an uncompromisable audit trail and log of all activities related to each sample batch, each rack and each sample. The manifest may be hashed at one or more levels.

In some embodiments, after receiving, scanning and updating the status of the racks and samples, a sample accessioning tech or lab tech may transfer the samples from the rack to a sample plate. The tech may need to open each sample tube, collect a portion of the sample held and transfer collected portion of the sample to a well in the sample plate. The transferring may be performed in same order as the tubes are positioned in the rack. For example, a rack that holds 94 sample tubes may be labelled with columns 1-12 and rows A-H. The labelling may be displayed on the rack itself or may be implicit and only used in the recordation of the position of sample tubes. The rack will not have open cells in the positions of A1 and A2, as these are reserved for control positive and control negative. The asymmetry of having a solid blank space on the upper left corner may be used to orient the rack during a computer vision analysis of the rack. The tech may collect and transfer a portion of the sample from sample tube at position C1 on the rack to well C1 on the sample plate. This process follows with collecting and transferring samples from D1-D1, E1-E1, F1-F1, G1-G1, H1-H1, A2-A2 . . . H12-H12. Well A1 may contain a control positive sample and well B1 may contain a control negative sample.

In some embodiments, each sample plate may be fed into the PCR machine for processing. Upon completion of the PCR run, the PCR curves produced for each sample may then be transferred to a database for storage and an analysis server to be analyzed. The status of the rack and samples held by the rack may be updated to show that the processing of the sample has been completed and that the results are being analyzed. Each sample curve may be analyzed by one or more machine learning models. The sample curves may also be processed to remove noise or enhance the curve results. The machine learning models may be trained on a data set of labelled PCR curves from previously analyzed results. The datasets may be generated by the analysis server itself, adding more samples after each batch of curves are analyzed. The datasets may also be generated synthetically by simulating testing scenarios and results. Datasets may also be obtained from other labs, universities or databases. The machine learning models may also be used to determine a confidence level of the classification of the PCR curves. A confidence threshold may be used to flag PCR curves that are not clearly discernable. The threshold may be set automatically by the system, be preset by an administrator or user of the system, be adjustable by a user or other machine learning or deep learning model or dynamically set based on the current batch of curves. If the confidence level of the analysis is at or above the specified threshold, the system may store the results locally and on the database. The record of the sample may then be updated with the analysis of the test results and the status of the sample. If the confidence level is below the specified threshold, the PCR curve for that sample may be flagged for review by the lab director or other lab personnel qualified to analyze and interpret PCR curve data. The sample curves that are flagged may be put into a queue for review by the lab director at a later time. The lab director may analyze the PCR curves and assign a positive or negative classification to them. The PCR curves may be displayed in a grid or gallery format, one at a time, a vertical or horizontal scroll, a swipe interface or other graphical user interface that allows a user to view one or more PCR curve graphs and make selections associated with those graphs. For example, the lab director may be displayed a single curve at a time or sets of curves. Sets of curves may be grouped chronologically, by priority, by confidence level or by any other sorting order. Sets that look similar to each other may also be grouped and displayed to the lab director at the same time. The curves may also be displayed in a visual representation of the sample plate, with the curves positioned at their position in the sample plate. The analysis may also be performed completely by the lab director.

The curve classification selection interface may include radio buttons for positive, negative, invalid and rerun. These radio buttons may be provided proximate to the curve they are associated with. A click based classification selection may also be used. For example, clicking on a curve once may set the classification to positive and highlight the graph/well in red (or other visual indication of a positive test result), clicking on a curve twice may set the classification to negative and highlight the graph/well in green (or other visual indication of a negative test result), clicking on a curve three times may set the classification to invalid and highlight the graph/well in yellow (or other visual indication of an invalid test result) and clicking on a curve four times may set the classification to rerun and highlight the graph/well in blue (or other visual indication of a sample that needs to be rerun).

FIG. 1 shows a diagram illustrating an exemplary environment of a sample collection, management and analysis system 100 in accordance with aspects of the present disclosure. The system 100 may comprise an analysis terminal 105, application server 110, analysis server 115, database 120, provider terminal 125, provider device 130, lab terminal 135, lab device 140, PCR system 145 and network 150.

Analysis terminal 105 may be an example of, or include aspects of, the corresponding element or elements described with reference to FIG. 2. Analysis terminal 105 may be one or more personal computers, personal digital assistants (PDAs), tablet computing devices, laptop computers, smart phones, e-readers or other systems capable of operating a standalone application or web-based application in a browser. Analysis terminal 105 may be in communication with one or more application servers 110, one or more analysis servers 115, one or more databases 120 and/or one or more lab terminals 135 through network 150.

Application server 110 may be an example of, or include aspects of, the corresponding element or elements described with reference to FIG. 3. Analysis server 115 may be an example of, or include aspects of, the corresponding element or elements described with reference to FIG. 4. Application server 110 and Analysis server 115 may be different machines, the same machine, virtual machines on different machines, virtual machines on the same machine, different machines at different locations or combination thereof, and connected to one another through network 150. Application server 110 and Analysis server 115 may be in communication with analysis terminal 105, database 120, provider terminal 125 and lab terminal 135 through network 150.

Lab terminal 135 may be an example of, or include aspects of, the corresponding element or elements described with reference to FIG. 5. Lab device 140 may be an example of, or include aspects of, the corresponding element or elements described with reference to FIG. 6.

PCR System 145 may be any PCR machine or sets of machines configured to system to amplify segments of DNA via the polymerase chain reaction (PCR). PCR system 145 may be any thermocycler, real-time PCR system, DNA amplification system, protein-misfolding cyclic amplification (PMCA) system, or other system configured to facilitate other temperature-sensitive reactions for rapid diagnostics. PMCA systems may be used for the detection of prions in the biological samples being tested. This may be used in the testing cattle for bovine spongiform encephalopathy (mad cow disease) and testing cattle feed for prions which may cause bovine spongiform encephalopathy. Similarly, this system may be used for the high throughput of testing for chronic wasting disease (CWD) in wild population of deer, elk, reindeer, sika deer and moose. Other industries that require large number of tests to be performed may also benefit from the disclosed system and methods, such as food manufacturing. Batch tests may be performed on samples from food manufacturing facilities to identify pathogens such as, Norovirus, *Salmonella, Clostridium perfringens, Campylobacter, Staphylococcus aureus* (Staph), *Clostridium botulinum* (botulism), *Listeria, Escherichia coli* (*E. coli*), *Vibrio, Cyclospora,* Hepatitis A and other foodborne pathogens.

Figure 2:
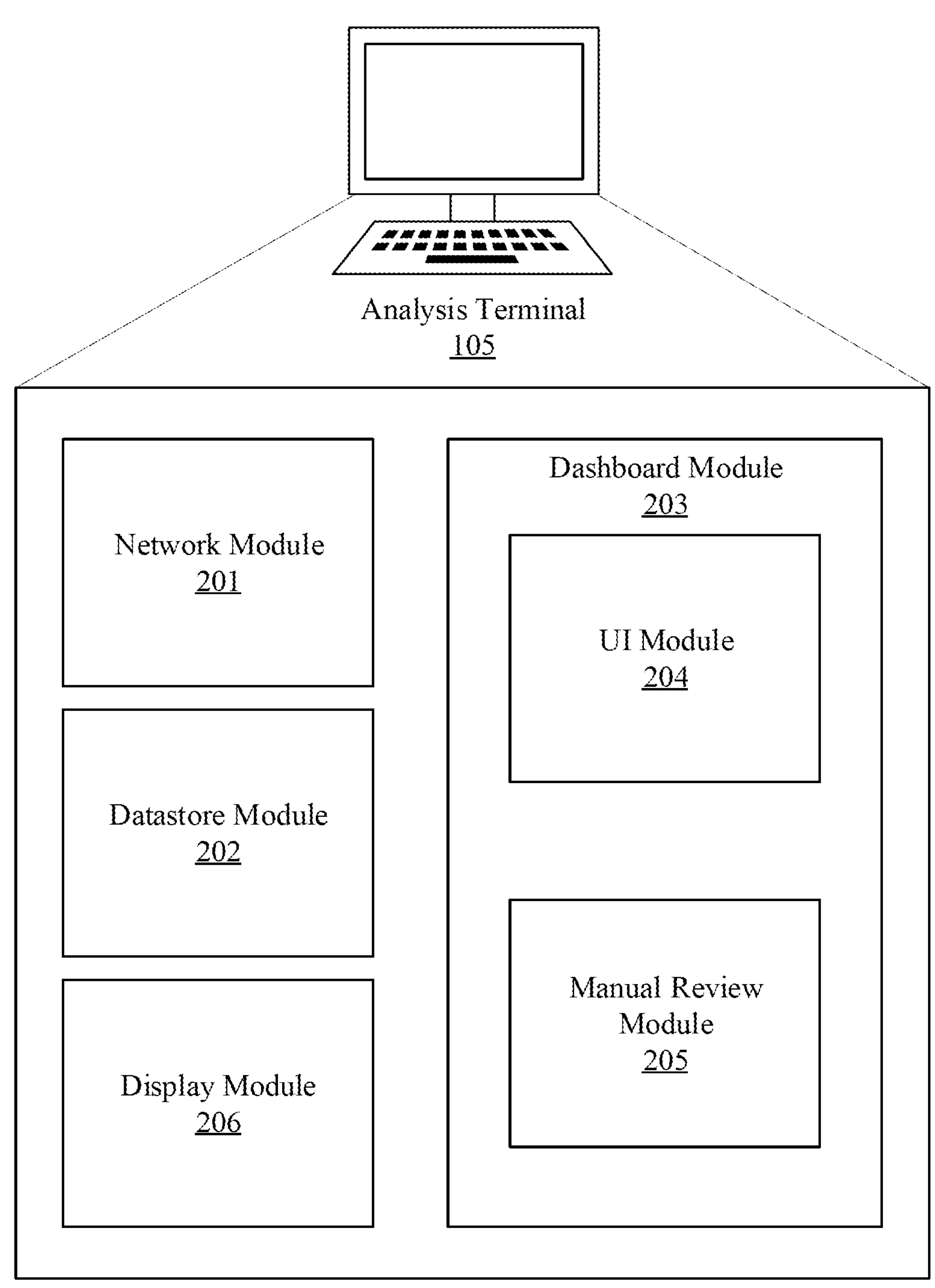
FIG. 2 is a diagram illustrating an exemplary analysis terminal in accordance with aspects of the present disclosure.

FIG. 2 is a diagram illustrating an exemplary analysis terminal 105 in accordance with aspects of the present disclosure. Analysis terminal 105 may comprise a network module 201, datastore module 202, dashboard module 203 and a display module 206.

Network module 201 may transmit and receive network signals and receive signals from other computing systems via a network. In some examples, the network module 201 may enable transmitting and receiving signals from the Internet. Signals received by the network module 201 may be used by the other modules. The modules may transmit signals through the network module 202.

Datastore module 202 may receive and serve information associated with patients, biological samples, batches of samples, racks holding sample tubes and other information necessary to manage, track, monitor, analyze or otherwise process collected biological samples. The datastore module 202 may retrieve and store information relating to a batch of samples collected at the provider facility, transferred to a destination facility and being processed by the PCR test 145 system. Each sample record created at the provider facility, including status/progress, location, patient ID, rack ID, batch ID, collection time, destination facility, test to be performed, sample tube barcode, sample tube QR code and/or other information related to the collected sample, may be received and stored by the datastore module 202. The sample records may be retrieved from application server 110, analysis server 115, database 120, lab terminal 125 or provider terminal 135. This information may be provided to the sample status tracking module 307 to facilitate the logging and tracking of each sample. The registration of each patient with a sample tube, the barcode/QR code on the sample tube, the biological sample, the results of the diagnostics performed on the sample and the progress/status of the sample throughout the process may be handled by the application server 110 and stored locally by the datastore module 302.

Dashboard module 203 may comprise UI module 204 and manual review module 205. Dashboard module 203 may manage the display UI components generated by the UI module 204. Dashboard module 203 may also manage the interaction of the lab director with the UI components and the manual review module 205.

UI module 204 may generate a user interface to allow the lab director or qualified lab tech to manage test results, select samples for additional analysis, select samples to be rerun, identify false positives and false negatives, view a queue of samples results to be analyzed/reviewed manually and/or view all results of a PCR run (PCR curves) visually, and superimposed over the samples location on a displayed sample plate map. The sample plate map may visually distinguish the samples which were unable to be classified by the machine learning models. For example, the PCR curves may be highlighted or surrounded by a box to identify the samples which require the attention of the lab director. The lab director may select any of the PCR curves to view a larger visualization of the curve.

In some embodiments, the visualization generated by the UI module 204 may be updated in real-time as the results of the PCR run become available. The lab director may view a sample plate map view which begins empty, and is filled with PCR curves as the results become available. In some embodiments, the display of the sample PCR curves may be displayed upon completion of the PCR run on all samples of the sample plate. The PCR curves may be received directly from the PCR machine or from the analysis server. The analysis server 115 may receive the results from the PCR run in the same manner as the UI module 204. The UI module 204 may also wait for the machine learning analysis to be performed by the analysis server 120 before displaying the PCR curves and analysis results to the lab director.

In some embodiments, the PCR curves may be displayed before the analysis is completed, and upon the classification of each PCR curve by the one or more machine learning models on the analysis server 115, the displayed PCR curves may be updated or modified to display the analysis results. The machine learning models may determine a confidence level of the classification of the PCR curves. A confidence threshold may be used to flag PCR curves that are not clearly discernable. For PCR curves with a confidence level below a predetermined confidence threshold, the PCR curve for that sample may be flagged for review by the lab director or other lab personnel qualified to analyze and interpret PCR curve data. The sample curves that are flagged may be put into a queue for review by the lab director at a later time.

The flagged PCR curves may be highlighted or otherwise visually differentiated from high confidence level PCR curves on the displayed plate map. The lab director may analyze the PCR curves and assign a positive or negative classification to them from the plate map visualization directly. In some embodiments, the PCR curves may be displayed in a grid or gallery format, one at a time, a vertical or horizontal scroll, a swipe interface or other graphical user interface that allows a user to view one or more PCR curve graphs and make selections associated with those graphs. For example, the lab director may be displayed a single curve at a time or sets of curves. Sets of curves may be grouped chronologically, by priority, by confidence level or by any other sorting order. Sets that look similar to each other may also be grouped and displayed to the lab director at the same time.

Manual review module 205 may be configured to alert a qualified user of an invalid analysis result or a result with a confidence level below the predetermined threshold. A qualified user may be the lab director or a lab tech trained on interpreting and analyzing PCR curves. Upon receiving the alert, the manual review module 205 may provide an interface to the qualified user for selecting a classification for each displayed result. The PCR curves may be displayed in a graphical user interface, with the PCR curve graph of each invalid or low confidence result disposed over the well position of the sample. In some embodiments, the invalid and low confidence results may be queued for analysis by the qualified user. The queued results may be grouped by similarity and displayed to the qualified user at the same time. The qualified user may be given the option to make a single classification selection to classify all of the results, make a classification selection for each result or select multiple results to include in a group classification selection to classify all the result of the selected results.

The manual review module 205 may include a radio button classification selection for positive, negative, invalid and rerun. These radio buttons may be provided proximate to the curve they are associated with. A click based classification selection may also be used. For example, clicking on a curve once may set the classification to positive and highlight the graph/well in red (or other visual indication of a positive test result), clicking on a curve twice may set the classification to negative and highlight the graph/well in green (or other visual indication of a negative test result), clicking on a curve three times may set the classification to invalid and highlight the graph/well in yellow (or other visual indication of an invalid test result) and clicking on a curve four times may set the classification to rerun and highlight the graph/well in blue (or other visual indication of a sample that needs to be rerun).

Display module 206 may be a touch-screen display, a head-up display, a head-mounted display, an optical see-through display, an optical see-around display, a video see-through display, a flat-panel display, a light-emitting diode (LED) display, an electroluminescent display (ELD), an electrophoretic display (EPD or electronic paper), a liquid crystal display (LCD), an organic LED (OLED) display, an active-matrix organic light-emitting diode display or any other type of display on a display device.

Figure 3:
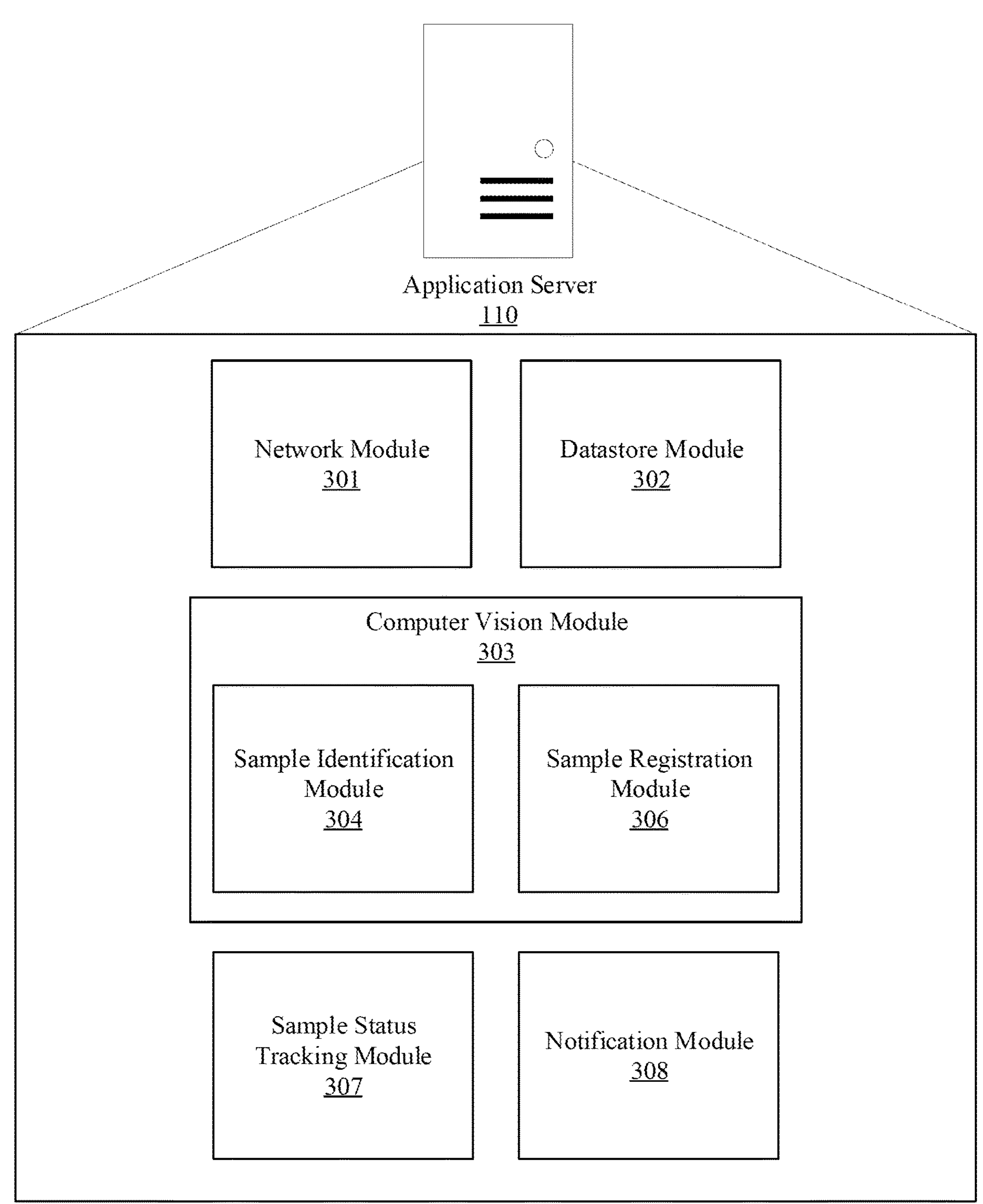
FIG. 3 is a diagram illustrating an exemplary application server in accordance with aspects of the present disclosure.

FIG. 3 is a diagram illustrating an exemplary application server 110 in accordance with aspects of the present disclosure. Application server 110 may comprise a network module 301, datastore module 302, computer vision module 303, sample status tracking module 307 and a notification module 308.

Network module 301 is similar in function to that of network module 201, and therefore not described in detail for sake of brevity.

Datastore module 302 may receive and serve information associated with patients, biological samples, batches of samples, racks holding sample tubes and other information necessary to manage, track, monitor otherwise process collected biological samples. The provider terminal 125 may provide information to the datastore module 302 relating to a batch of samples collected at the provider facility and being transferred to a destination facility for processing. Each sample record created at the provider facility, including status/progress, location, patient ID, rack ID, batch ID, collection time, destination facility, test to be performed, sample tube barcode, sample tube QR code and/or other information related to the collected sample, may be received and stored by the datastore module 302. This information may be provided to the sample status tracking module 307 to facilitate the logging and tracking of each sample. The registration of each patient with a sample tube, the barcode/QR code on the sample tube, the biological sample, the results of the diagnostics performed on the sample and the progress/status of the sample throughout the process may be handled by the application server 110 and stored locally by the datastore module 302. A local copy of the data associated with the biological samples currently registered in the system may be stored from the initial registration of the patient with a sample tube before collection, until the results have been provided to the patient and stored locally on the Analysis terminal 105.

Computer vision module 303 may comprise a sample identification module 304, visual tracking module 305 and sample registration module 306. The computer vision module 303 may be implemented on the application server 110, provider terminal 125, provider device 130, lab terminal 135, lab device 140 or combination thereof. The computer vision module 303 may receive one or more images of one or more racks. The images may be captured at the provider facility or at the destination facility. At the capturing device, a provider/nurse/lab tech may capture one or more images or video of one or more racks. The provider may select and drag a bounding box a displayed image to provide an orientation and region of interest to be analyzed. A rectangular region may also be displayed on the device in which the provider must align the rack with the box before an image may be captured. These images and/or videos are then processed by the computer vision module 303.

Sample identification module 304 may analyze the one or more images of each rack to identify the orientation of the rack within the captured images if the orientation has not already been specified by the provider or lab technician. The sample identification module 304 may further identify one or more test tubes held by the rack, drawing a bounding sub-box around each sample and extracting and analyzing each of the regions of interest contained within each sub-box to further identify a QR code affixed to the top (lid) of a sample tube/test tube. The identified QR codes may then be read for each identified test tube and the test tube may then be associated/registered, by the sample registration module 306, with a patient based on the read QR code. The association and registration of the patient with their sample, the sample with the test tube and the test tube with the rack may then be tracked and monitored by the sample status tracking module 307 and/or otherwise stored in the provider terminal 125, provider device 130, lab terminal 135 and/or lab device 140.

If the sample identification module 304 is unable identify a sample tube and the affixed QR code from the one or more images, the provider or lab technician may be prompted to recapture an image of the entire rack to attempt the analysis, identification and registration again.

In some embodiments, the provider or lab tech may capture one or more images of the rack and sample tubes held by the rack from a closer position. The images may also be captured at a higher magnification level or zoomed-in on. The image may not include the entire rack, but only the sample tubes unable to be identified and those in close proximity to it. The identification of the position of the sample tube of interest may be determined based on the identification of the previously identified sample tubes proximate to the unidentifiable sample tube. The system may then analyze the portion of the image in the identified position to recognize the QR code of the previously unidentifiable sample tube.

In some embodiments, the provider or lab tech may remove the unidentifiable sample tube and capture an image of the QR code on top of the unidentifiable sample tube or the barcode on the side of the unidentifiable sample tube. A provider or lab tech may also use a handheld or stationary barcode/QR code scanner to register the unidentifiable sample tube.

After removing the unidentifiable sample tube, the lab technician may also manually enter an ID number or other information from the barcode or other labels on the unidentifiable sample tube.

Sample status tracking module 307 may receive status updates from provider terminals and/or provider devices upon scanning of the sample tubes and registering of the tubes in the one or more racks. The provider terminal may also send updates on the status of racks, batches of racks, and individual samples held in sample tubes held by the racks when not only capturing images of the racks for registration, but also upon initiating a transfer of the batch of racks from the provider facility to the destination facility and upon the physical handoff from the provider to a courier service to carry out the transfer. The sample status tracker module 307 may also access external servers, databases, applications, websites and/or APIs to receive updated information from the courier service or other third parties that may handle the racks between the provider facility and the destination facility. Upon arrival of the racks at the destination facility, the scanning and imaging of the racks and the sample tubes held in each rack may trigger an update to be sent directly to the sample status tracking module 307. This may happen if the sample identification and registration is performed at the lab terminal 135. If the captured images are sent to the application server for identification and registration, the sample status tracking module may instead receive the status update information from the computer vision module 303 or the data store module 302.

In some embodiments, the analysis server 115 may provide status information to the sample status tracking module 307. The updates from the analysis server 115 may include the analysis and results of the diagnostic tests (positive, negative or invalid) as well as the progress (completed, processing, sample being rerun).

Notification Module 308 may relay updates received by the sample status tracking module 307 to patient devices, lab terminals, and provider terminals. The notification may be displayed to the lab director, lab techs, providers and patients, providing a direct link to the associated information in a dashboard or portal interface.

Figure 4:
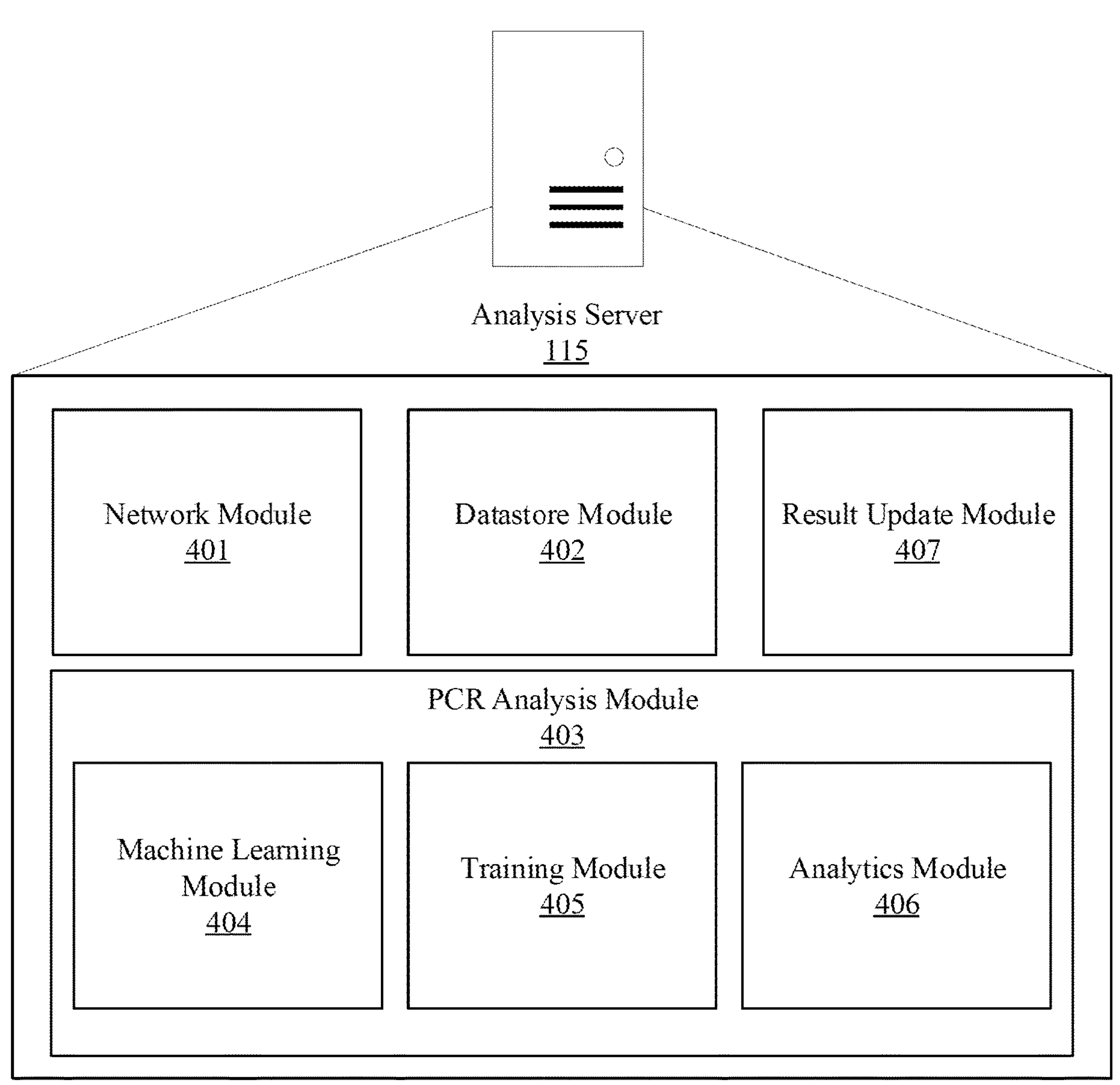
FIG. 4 is a diagram illustrating an exemplary analysis server in accordance with aspects of the present disclosure.

FIG. 4 is a diagram illustrating an exemplary analysis server 115 in accordance with aspects of the present disclosure. Analysis server 115 may comprise network module 401, datastore module 402, PCR analysis module 403 and result update module 408. Network module 401 and datastore module 402 are similar to the network module 301 and datastore module 302 of FIG. 3 and will not be described in detail for the sake of brevity.

PCR analysis module 403 may comprise a machine learning module 404, training module 405 and an analytics module 406. The PCR analysis module 403 may be responsible for the automated analysis of results received from PCR test 145 systems at one or more destination labs. A large number of labs and PCR systems may use a single analysis server. Clusters of analysis servers may also be used to process the PCR curves received from a plurality of labs.

The PCR analysis module 403 provides the received PCR curve data to the machine learning module 404. The machine learning module 404 may use one or more machine learning modules to analyze the received PCR curves and to classify the results of the curves. The machine learning module 404 may also be configured to calculate a confidence level for each PCR curve classified. Results with a confidence level at or above a predetermined threshold level may be considered accurate. Each accurate result may be associated/linked/added to a patients record and updated on in the database and the application server 110 by the result update module 407.

The machine learning module 405 may comprise decision trees such as classification trees, regression trees, boosted trees, bootstrap aggregated decision trees, random forests, rotation forests or a combination thereof. Additionally or alternatively, the machine learning module 405 may comprise neural networks such as, artificial neural networks (ANN), autoencoders, probabilistic neural networks (PNN), time delay neural networks (TDNN), convolutional neural networks (CNN), deep stacking networks (DSN), radial basis function networks (RBFN), general regression neural networks (GRNN), deep belief networks (DBN), deep neural networks (DNN), deep reinforcement learning (DRL), recurrent neural networks (RNN), fully recurrent neural networks (FRNN), Hopfield networks, Boltzmann machines, deep Boltzmann machines, self-organizing maps (SOM), learning vector quantizations (LVQ), simple recurrent networks (SRN), reservoir computing, echo state networks (ESN), long short-term memory networks (LSTM), bi-directional RNNs, hierarchical RNNs, stochastic neural networks, genetic scale models, committee of machines (CoM), associative neural networks (ASNN), instantaneously trained neural networks (ITNN), spiking neural networks (SNN), regulatory feedback networks, neocognitron networks, compound hierarchical-deep models, deep predictive coding networks (DPCN), multilayer kernel machines (MKM), cascade correlation networks (CCN), neuro-fuzzy networks, compositional pattern-producing networks, one-shot associative memory models, hierarchical temporal memory (HTM) models, holographic associative memory (HAM), neural Turing machines, or combination thereof.

A NN may be a hardware or a software component that includes a number of connected nodes (a.k.a., artificial neurons), which may be seen as loosely corresponding to the neurons in a human brain. Each connection, or edge, may transmit a signal from one node to another (like the physical synapses in a brain). When a node receives a signal, it can process the signal and then transmit the processed signal to other connected nodes. In some cases, the signals between nodes comprise real numbers, and the output of each node may be computed by a function of the sum of its inputs. Each node and edge may be associated with one or more node weights that determine how the signal is processed and transmitted.

Training module 405 may be configured to train one or more machine learning, deep learning and/or artificial intelligence models. The curves in the training datasets may be processed to remove noise or enhance the curve results. The machine learning models may be trained on a data set of labelled PCR curves from previously analyzed results. The datasets may be generated by the analysis server itself, adding more samples after each batch of curves are analyzed. The datasets may also be generated synthetically by simulating testing scenarios and results. Datasets may also be obtained from other labs, universities or databases. The training of the machine learning models may be supervised, unsupervised or semi-supervised.

During the training process, the training module 405 may adjust one or more node weights to improve the accuracy of the result (i.e., by minimizing a loss function which corresponds in some way to the difference between the current result and the target result). The weight of an edge may increase or decrease the strength of the signal transmitted between nodes. In some cases, nodes may have a threshold below which a signal is not transmitted at all. The nodes may also be aggregated into layers. Different layers may perform different transformations on their inputs. The initial layer may be known as the input layer and the last layer may be known as the output layer. In some cases, signals may traverse certain layers multiple times.

The analytics module 406 may also receive the results of the analysis, with or without attached patient information. When stored without the associated patient information, the analysis data may be used in an anonymized manner to protect the identity of the patient.

Figure 5:
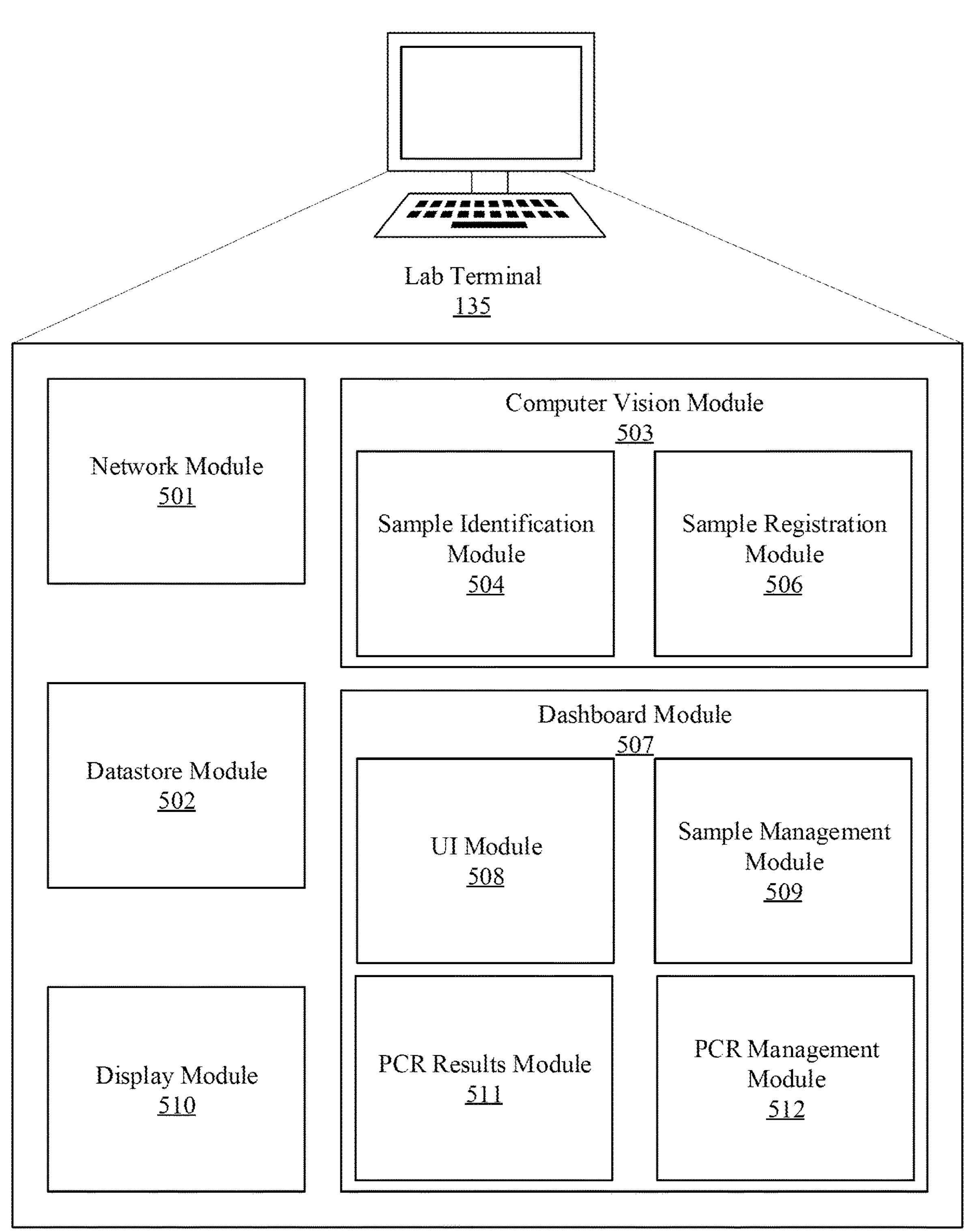
FIG. 5 is a diagram illustrating an exemplary lab terminal in accordance with aspects of the present disclosure.

FIG. 5 is a diagram illustrating an exemplary lab terminal 135 in accordance with aspects of the present disclosure. Lab terminal 135 may comprise network module 501, datastore module 502, computer vision module 503, sample identification module 504, sample registration module 506, dashboard module 507, UI module 508, sample management module 509, display module 510, PCR results module 511 and PCR management module 512.

The network module 501, datastore module 502 computer vision module 503, sample identification module 504, sample registration module 506 and display module 710 may be similar in function to that of network module 301, datastore module 302, computer vision module 303, sample identification module 304, sample registration module 306 and display module 310 and therefore not described in detail for sake of brevity.

Dashboard module 507 may comprise UI module 508, sample management module 509, PCR results module 511 and PCR management module 512. The dashboard module 507 may manage display of UI components generated by UI module 508. A dashboard, terminal or portal may display information relating to the one or more racks received at the destination lab. The dashboard module 507 may also organize samples received as individual samples tubes holding collected samples from patients or provider facilities, samples aggregated and held in one or more racks, and samples received in bags or other containers from one or more provider facilities.

Sample management module 509 may receive manifest or other information relating to the racks, sample tubes, patients, and batches of samples received at the destination lab. Upon receiving the one or more racks of samples from one or more provider facilities, the lab tech may scan each rack to verify the receipt of the sample batch. Sample management module, may update status and progress information for each received sample. After transferring samples from each rack to a sample plate, the sample management module may register the samples to the specific sample plate and to the PCR run processed for that plate.

The PCR results module 511 may retrieve, format and display the results on the display 510. The PCR results module may also send and receive results for each sample and each rack to the provider terminal 125.

PCR management module 512 may control the PCR machine itself. The PCR management module may initiate the processing of one or more plates after having the samples transferred from the racks. One or more plates may be loaded or queued to be loaded and processed by one or more PCR machines. The PCR management module may also transfer the PCR results from the PCR machine to the analysis server 115.

Figure 6:
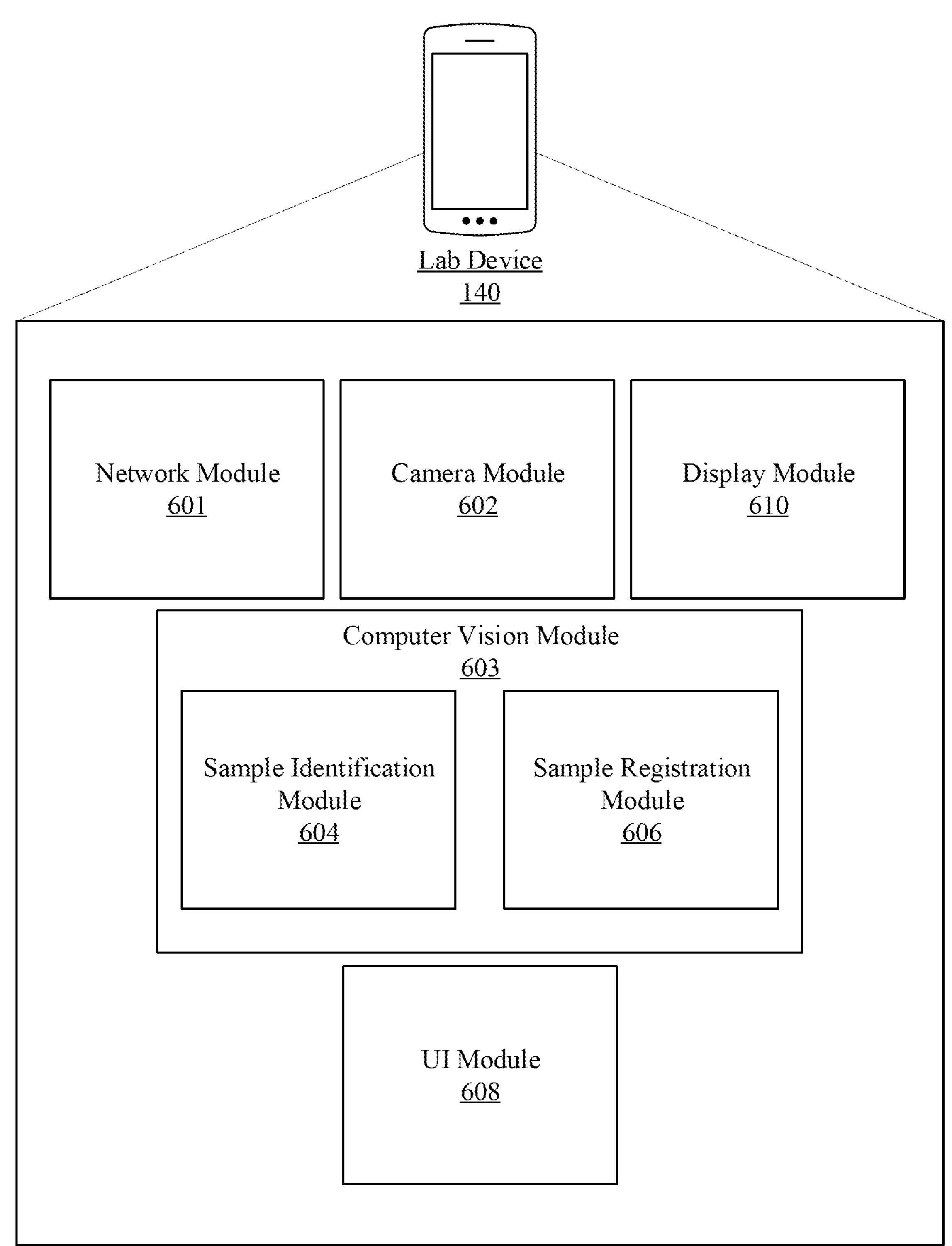
FIG. 6 is a diagram illustrating an exemplary lab device in accordance with aspects of the present disclosure.

FIG. 6 is a diagram illustrating an exemplary lab device 140 in accordance with aspects of the present disclosure. Lab device 140 may comprise a network module 601, camera module 602, computer vision module 603, sample identification module 604, sample registration module 606, UI module 608 and display module 610.

The network module 601, computer vision module 603, sample identification module 604, sample registration module 606, UI module 608 and display module 610 may be similar in function to that of network module 501, computer vision module 503, sample identification module 504, sample registration module 506, UI module 508 and display module 510 and therefore not described in detail for sake of brevity.

Camera module 602 may comprise any camera or combination of cameras configured to record images. The cameras may be any type of image sensor which provides an image of a scene viewed from the viewpoint of the device, or user, or both. The cameras may be any device configured to detect visible light (e.g. CCD or CMOS based cameras) or light of other spectrums (e.g. multi-spectral or hyper-spectral cameras), such as infrared, ultraviolet, x-rays or any other wavelength the device is capable of detecting. Other types of cameras are possible as well, such as a time-of-flight camera, stereoscopic cameras or other camera combinations capable of determining depth of a captured image/video. The camera module 602 may include hardware, or software, or both, to enable the use of structured light depth determination or time-of-flight depth determination. Camera module 602 may also be a combination of two or more of the devices described above.

FIGS. 7A-7C are diagrams illustrating an exemplary tube rack in accordance with aspects of the present disclosure. tube rack 700 may comprise a rack control blank 701 and receptacles for one or more sample tubes 702. Rack 700 may be of any dimension that corresponds to the dimensions of the sample trays for which the samples are to be transferred to. The rack may be 3D printed, injection molded or otherwise manufactured from plastic or resins. Bioplastics and compostable materials as well as composite materials may also be used in the construction of the rack and rack cover (not shown). A rack cover may fit over or around the rack to protect the sample tubes during transport or storage. The rack may also be designed to slide into an enclosure. Covers and enclosures may also be designed to carry and store multiple racks at one time. There may be individual shelves used to hold each individual rack or an opening may be large enough to hold a plurality of racks stacked on one another. The racks may also include recesses and protrusions on the top and bottoms of the racks to allow for the racks to be securely stacked. The underside of each rack may also comprise regions designed to secure sample tubes of the rack below. For example, the bottom of each rack may have a circular indention which matches the sample tube lid, allowing for each sample to be secured by the rack stacked on top of them.

Sample tube 702 may be any sample tube with dimensions that fit into the slots or rack 700. FIG. 7B is a diagram illustrating an exemplary sample tube in accordance with aspects of the present disclosure. Sample tube 702 may have a QR code printed on the affixed lid. The QR code may be used by the provider device 130 and lab device 140 in the identifying, scanning, registration and verification of samples held in the racks 700. As shown in FIG. 7C, sample tube 702 may also include a barcode and label affixed to the side of the body of the tube. This barcode may also be used by provider and lab techs to identify samples when a scan of the QR code fails.

Figure 8A:
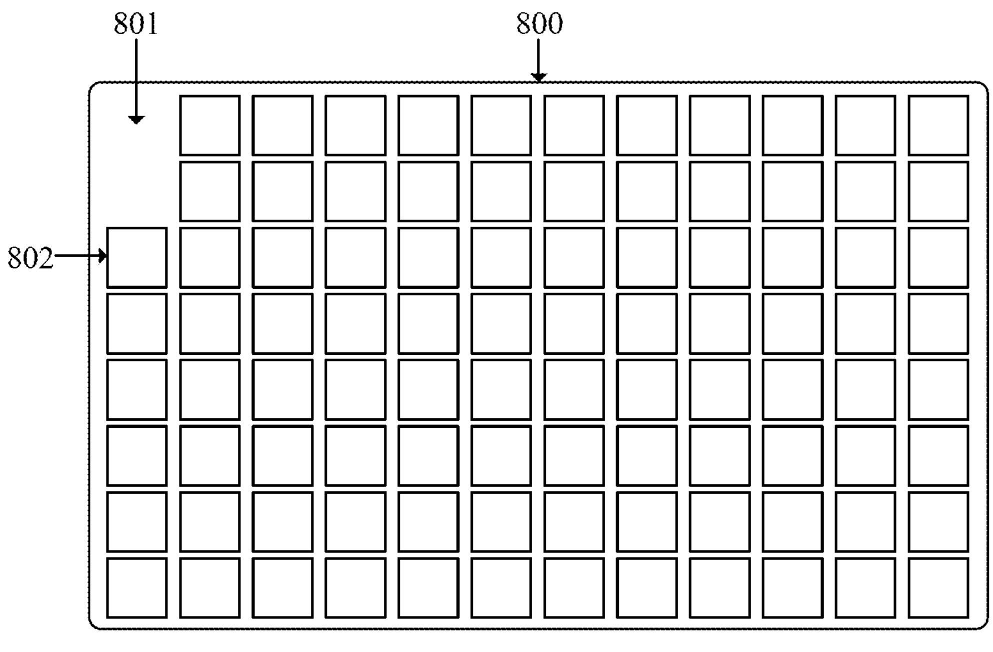
FIG. 8A is a diagram illustrating an exemplary tube rack in accordance with aspects of the present disclosure.

FIG. 8A is a diagram illustrating an exemplary tube rack 800 in accordance with aspects of the present disclosure. Tube rack 800 may comprise a rack control blank region 801 and sample tube cells/receptacles 802. The rack control blank region may be marked or otherwise distinguished from other parts of the rack. The area may also be left blank and without a sample cell to indicate that the corresponding sample wells of the sample plate are reserved for positive control and negative control samples. The rack control blank region 801 provides a landmark for determining orientation and positioning of the racks when capturing images of the rack and sample tubes held by the rack. This may greatly help in the identifying of sample tubes in the captured image and the drawing of bounding boxes around the sample tube regions to be extracted and analyzed.

Figure 8B:
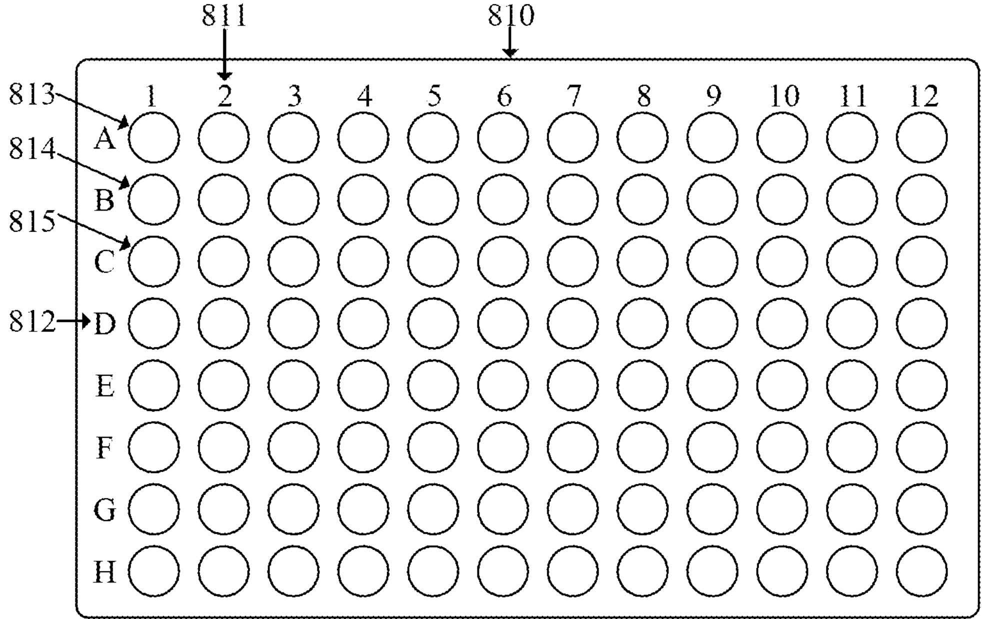
FIG. 8B is a diagram illustrating an exemplary sample tray in accordance with aspects of the present disclosure.

FIG. 8B is a diagram illustrating an exemplary sample tray 810 in accordance with aspects of the present disclosure. sample tray 810 may comprise tray columns 811, tray rows 812, positive control sample 813, negative control sample 814 and first test sample 815.

Figure 9:
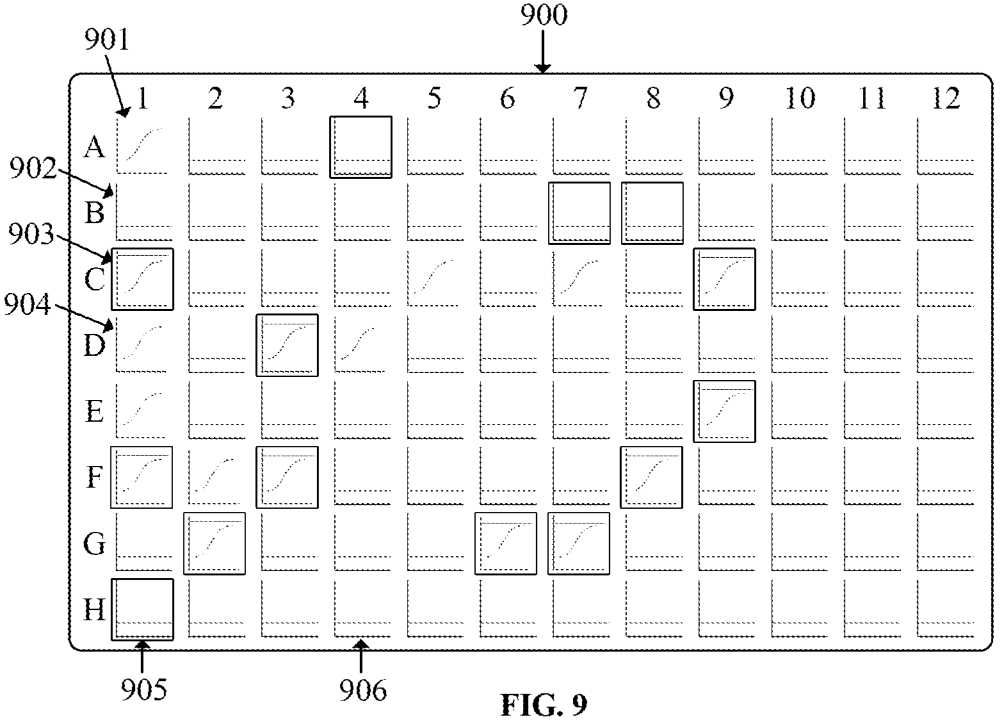
FIG. 9 is a diagram illustrating an exemplary analysis interface view in accordance with aspects of the present disclosure.

FIG. 9 is a diagram illustrating an exemplary analysis interface 900 view in accordance with aspects of the present disclosure. Analysis interface 900 may comprise representations of PCR curves of each sample processed. Control positive 901 and control negative 902 are in position A1 and B1. Each PCR curve graph represents the result received from the PCR test 145 system, lab terminal 135 and/or analysis server 115. The interface may be generated by dashboard module 203, UI module 204, manual review module 205 or combination thereof. The generated analysis interface 900 may be displayed on analysis terminal 105 through display module 206.

In some embodiments, after a sample tray has been processed by a PCR machine, a PCR curve is generated for each sample. These PCR curves may be sent to the analysis server 115 to be analyzed by one or more machine learning models. The machine learning models may determine a classification for each PCR curve received from the PCR machine and send that classification to the analysis terminal 105 for visualization. Sample PCR curves that have been analyzed by the machine learning models and have a confidence level below a predetermined threshold may be displayed with a visual indication that the PCR curve needs manual analysis by the lab director. For example, false positive 903 at C1 and false negative 905 at H1 are displayed within a box, but may also be highlighted, a different color, depth or other visually distinguishing manner. Samples PCR curves that have been analyzed by the machine learning models and have a confidence level at or above the predetermined threshold may be displayed without any distinguishing marks or indications. For example, true positive 904 at D1 and true negative 906 at H4 are displayed without any highlighting or bounding box.

The sample PCR curves that require manual analysis may be analyzed and classified from the analysis interface through input from the lab director or qualified user. The classification may be based on a number of clicks on the PCR curve that the lab director is analyzing and intends to classify. A selection menu may also be displayed over each PCR curve by default, upon scrolling over the PCR curve or as a result of clicking/selecting the PCR curve of interest.

Figure 10:
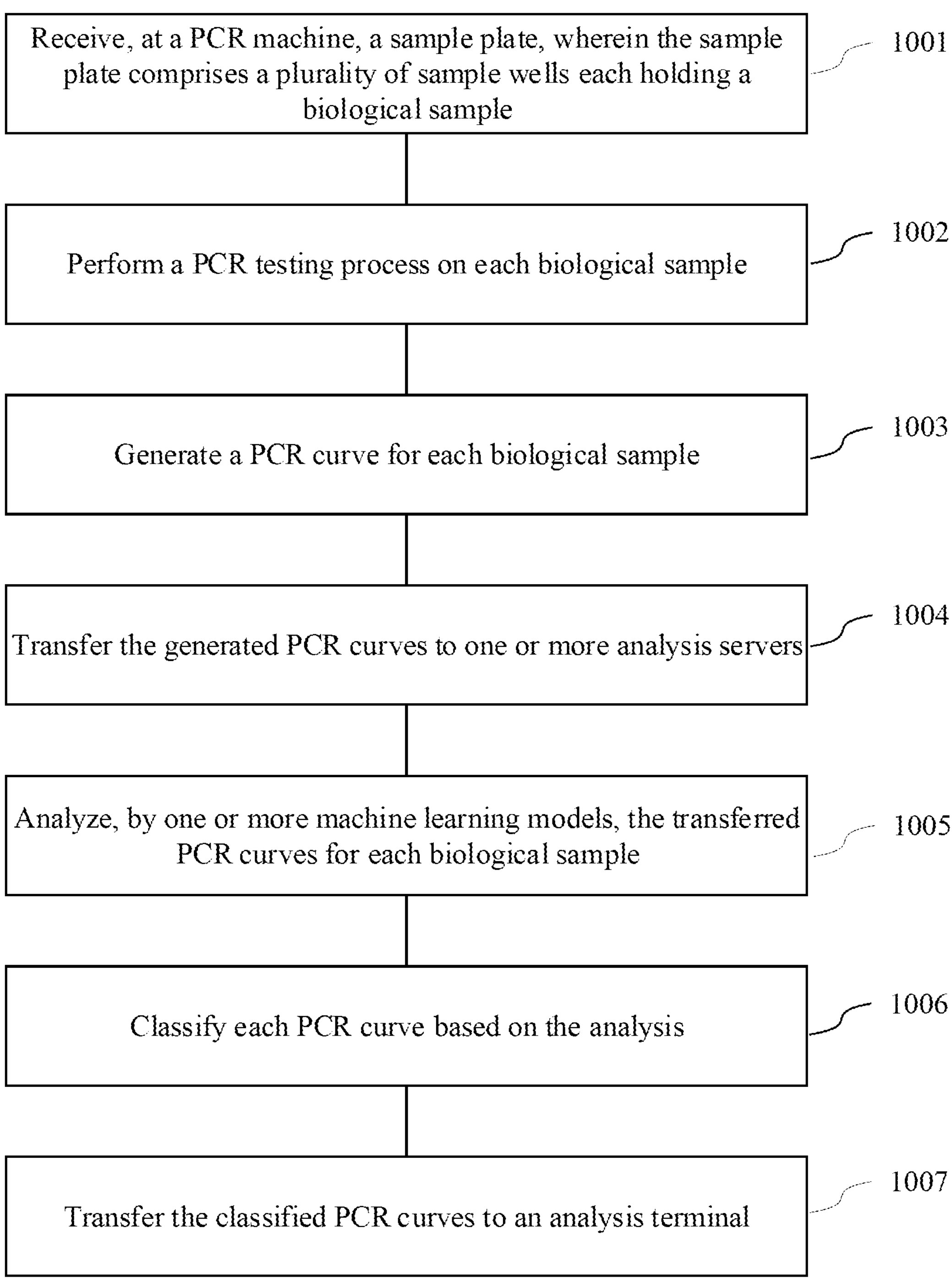
FIG. 10 is a flow chart illustrating an exemplary method that may be performed in accordance with some embodiments.

FIG. 10 is a flow chart illustrating an exemplary method 1000 that may be performed in accordance with some embodiments.

At step 1001, the system is configured to receive, at a PCR machine, a sample plate, wherein the sample plate comprises a plurality of sample wells each holding a biological sample At step 1002, the system is configured to perform a PCR testing process on each biological sample.

At step 1003, the system is configured to generate a PCR curve for each biological sample.

At step 1004, the system is configured to transfer the generated PCR curves to one or more analysis servers.

At step 1005, the system is configured to analyze, by one or more machine learning models, the transferred PCR curves for each biological sample.

At step 1006, the system is configured to classify each PCR curve based on the analysis.

At step 1007, the system is configured to transfer the classified PCR curves to an analysis terminal.

Figure 11:
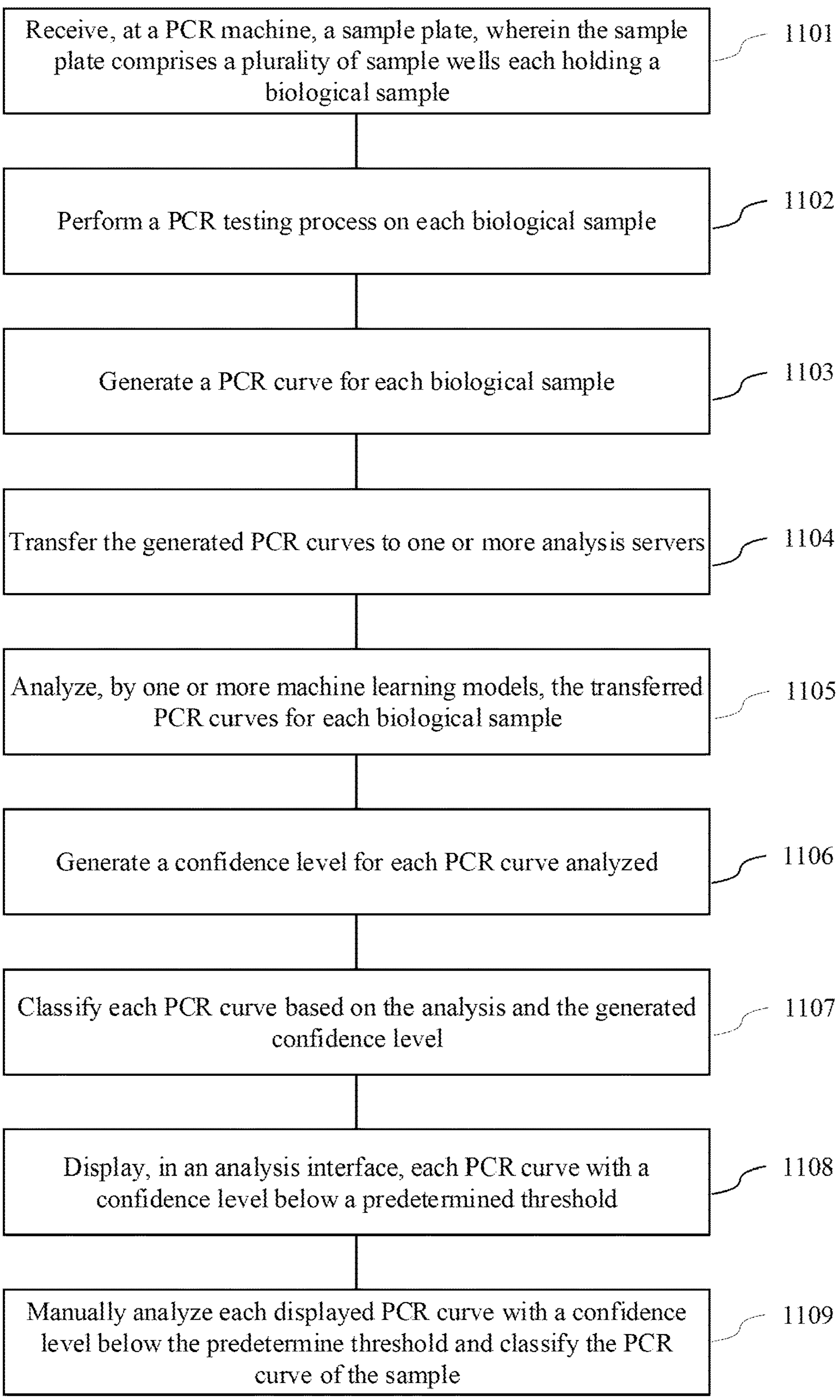
FIG. 11 is a flow chart illustrating an exemplary method that may be performed in accordance with some embodiments.

FIG. 11 is a flow chart illustrating an exemplary method 1100 that may be performed in accordance with some embodiments.

At step 1101, the system is configured to receive, at a PCR machine, a sample plate, wherein the sample plate comprises a plurality of sample wells each holding a biological sample.

At step 1102, the system is configured to perform a PCR testing process on each biological sample.

At step 1103, the system is configured to generate a PCR curve for each biological sample.

At step 1104, the system is configured to transfer the generated PCR curves to one or more analysis servers.

At step 1105, the system is configured to analyze, by one or more machine learning models, the transferred PCR curves for each biological sample.

At step 1106, the system is configured to generate a confidence level for each PCR curve analyzed.

At step 1107, the system is configured to classify each PCR curve based on the analysis and the generated confidence level.

At step 1108, the system is configured to display, in an analysis interface, each PCR curve with a confidence level below a predetermined threshold.

At step 1109, the system is configured to manually analyze each displayed PCR curve with a confidence level below the predetermine threshold and classify the PCR curve of the sample.

Figure 12:
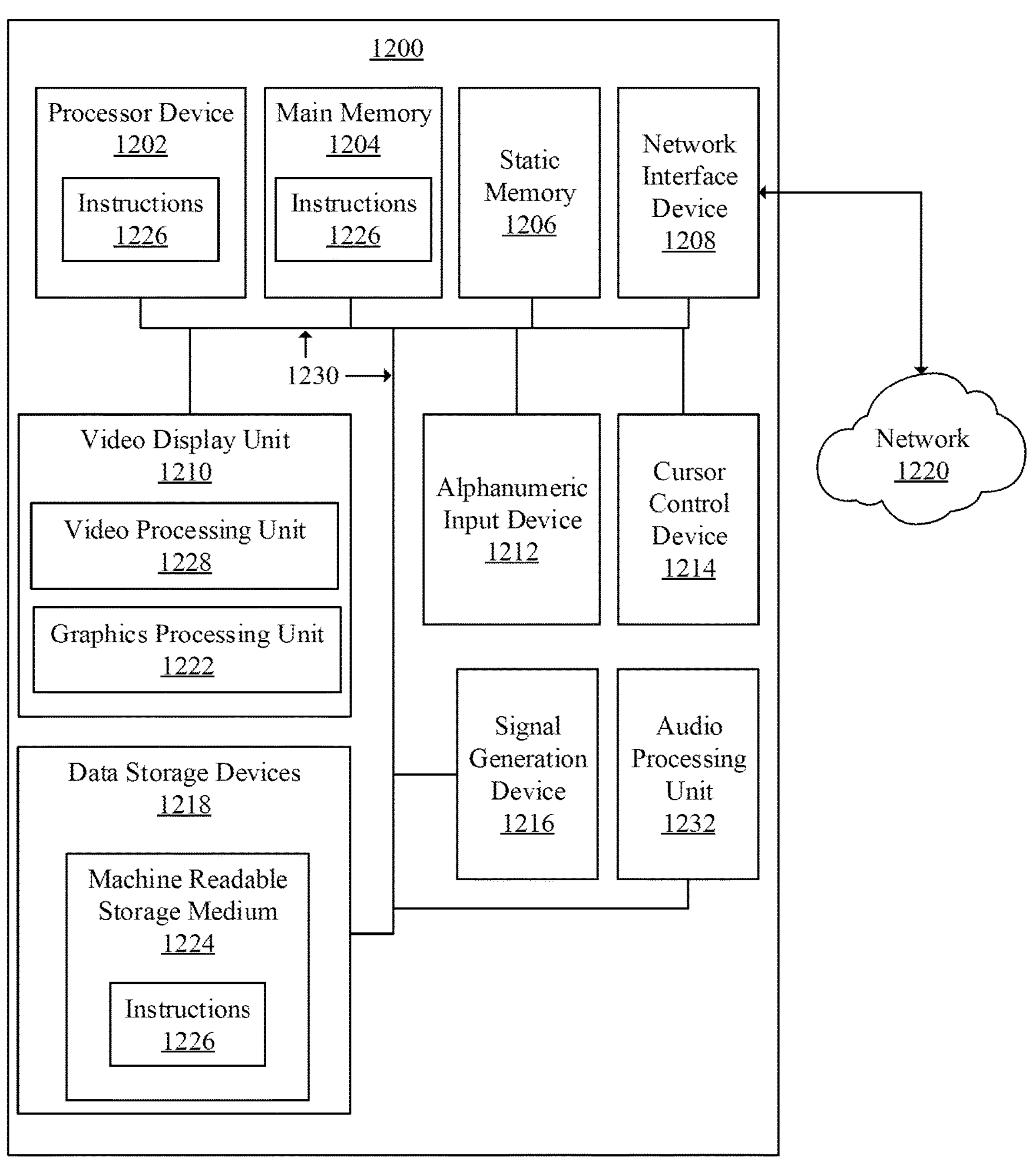
FIG. 12 is a diagram illustrating an exemplary computer that may perform processing in some embodiments and in accordance with aspects of the present disclosure.

FIG. 12 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 1200 includes a processing device 1202, a main memory 1204 (e.g., read-only memory (ROM), flash memory, dynamic random access memory (DRAM) such as synchronous DRAM (SDRAM) or Rambus DRAM (RDRAM), etc.), a static memory 1206 (e.g., flash memory, static random access memory (SRAM), etc.), and a data storage device 1218, which communicate with each other via a bus 1230.

Processing device 1202 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. The processing device 1202 is configured to execute instructions 1226 for performing the operations and steps discussed herein.

The computer system 1200 may further include a network interface device 1208 to communicate over the network 1220. The computer system 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse), a graphics processing unit 1222, a signal generation device 1216 (e.g., a speaker), graphics processing unit 1222, video processing unit 1228, and audio processing unit 1232.

The data storage device 1218 may include a machine-readable storage medium 1224 (also known as a computer-readable medium) on which is stored one or more sets of instructions or software 1226 embodying any one or more of the methodologies or functions described herein. The instructions 1226 may also reside, completely or at least partially, within the main memory 1204 and/or within the processing device 1202 during execution thereof by the computer system 1200, the main memory 1204 and the processing device 1202 also constituting machine-readable storage media.

In one implementation, the instructions 1226 include instructions to implement functionality corresponding to the components of a device to perform the disclosure herein. While the machine-readable storage medium 1224 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A system for analyzing biological samples, the system comprising:

an analysis terminal comprising:
- at least one processor operatively connected to a memory;
- a network module;
- one or more input devices; and
- a display;

one or more analysis servers comprising:
- at least one processor operatively connected to a memory;
- a network module; and
- one or more machine learning modules, trained to classify PCR curves of biological samples;
- a database, operatively connected to the analysis terminal and the one or more analysis servers;

one or more polymerase chain reaction (PCR) systems, the one or more PCR systems are configured to:
- receive a sample plate, wherein the sample plate comprises a plurality of sample wells each holding a biological sample, wherein the sample plate comprises a positive control sample and a negative control sample, and wherein the sample plate comprises multiple labeled rows and multiple labeled columns;
- perform a PCR testing process on each biological sample included in the sample plate;
- generate a PCR curve for each biological sample; and
- transfer the generated PCR curves to the one or more analysis servers;

the one or more analysis servers are configured to:
- receive the generated PCR curves from the one or more PCR systems;
- analyze, by the one or more machine learning models, the received PCR curves for each biological sample;
- classify each PCR curve based on the analysis;
- transfer the classified PCR curves to the analysis terminal; and
- providing for display, via the analysis terminal, a user interface depicting a representation of the sample plate with a graphical representation of the generated PCR curves being depicted at multiple row and column locations, wherein a graphical representation of a first PCR curve for the positive control sample is depicted and a graphical representation of a second PCR curve for the negative control sample is depicted.

2. The system of claim 1, wherein the one or more machine learning models are configured to assign a confidence level to each received PCR curve; and wherein the classifying each PCR curve is further based on the assigned confidence level.

3. The system of claim 2, wherein each PCR curve is classified as true positive, true negative, false positive, false negative, or unknown.

4. The system of claim 2, wherein a qualified user is alerted for each PCR curve with a confidence level below a predetermined threshold.

5. The system of claim 4, wherein the analyzing of each PCR curve with a confidence level below the predetermined threshold is analyzed by the qualified user.

6. The system of claim 2, wherein each PCR curve with a confidence level at or above a predefined threshold is classified as a true positive or true negative.

7. A computer implemented method for analyzing biological samples, method comprising:

receiving, at a polymerase chain reaction (PCR) machine, a sample plate, wherein the sample plate comprises a plurality of sample wells each holding a biological sample, wherein the sample plate comprises a positive control sample and a negative control sample, and wherein the sample plate comprises multiple labeled rows and multiple labeled columns;

performing a PCR testing process on each biological sample in the sample plate;

generating a PCR curve for each biological sample; and transferring the generated PCR curves to one or more analysis servers, wherein the one or more analysis servers are configured to:

receive the generated PCR curves from the PCR machine;

analyze, by one or more machine learning models, the received PCR curves for each biological sample;

classify each PCR curve based on the analysis;

transfer the classified PCR curves to an analysis terminal; and providing for display, via the analysis terminal, a user interface depicting a representation of the sample plate with a graphical representation of the generated PCR curves being depicted at multiple row and column locations, wherein a graphical representation of a first PCR curve for the positive control sample is depicted and a graphical representation of a second PCR curve for the negative control sample is depicted.

8. The computer implemented method of claim 7, wherein the one or more machine learning models are configured to assign a confidence level to each received PCR curve; and wherein the classifying each PCR curve is further based on the assigned confidence level.

9. The computer implemented method of claim 8, wherein each PCR curve is classified as true positive, true negative, false positive, false negative, or unknown.

10. The computer implemented method of claim 8, wherein a qualified user is alerted for each PCR curve with a confidence level below a predetermined threshold.

11. The computer implemented method of claim 10, wherein the analyzing of each PCR curve with a confidence level below the predetermined threshold is analyzed by the qualified user.

12. The computer implemented method of claim 8, wherein each PCR curve with a confidence level at or above a predefined threshold is classified as true positive or true negative.

13. A Non-transitory computer-readable medium that stores executable program instructions that, when executed by one or more computing devices, configure the one or more computing devices to perform operations comprising:

receiving, at a polymerase chain reaction (PCR) machine, a sample plate, wherein the sample plate comprises a plurality of sample wells each holding a biological sample, wherein the sample plate comprises a positive control sample and a negative control sample, and wherein the sample plate comprises multiple labeled rows and multiple labeled columns;

performing a PCR testing process on each biological sample in the sample plate;

generating a PCR curve for each biological sample; and transferring the generated PCR curves to one or more analysis servers, wherein the one or more analysis servers are configured to:

receive the generated PCR curves from the PCR machine;

analyze, by one or more machine learning models, the received PCR curves for each biological sample;

classify each PCR curve based on the analysis;

transfer the classified PCR curves to an analysis terminal; and providing for display, via the analysis terminal, a user interface depicting a representation of the sample plate with a graphical representation of the generated PCR curves being depicted at multiple row and column locations, wherein a graphical representation of a first PCR curve for the positive control sample is depicted and a graphical representation of a second PCR curve for the negative control sample is depicted.

14. The non-transitory computer-readable medium of claim 13, wherein the one or more machine learning models are configured to assign a confidence level to each received PCR curve; and wherein the classifying each PCR curve is further based on the assigned confidence level.

15. The non-transitory computer-readable medium of claim 14, wherein each PCR curve is classified as true positive, true negative, false positive, false negative, or unknown.

16. The non-transitory computer-readable medium of claim 14, wherein a qualified user is alerted for each PCR curve with a confidence level below a predetermined threshold.

17. The non-transitory computer-readable medium of claim 16, wherein the analyzing of each PCR curve with a confidence level below the predetermined threshold is analyzed by the qualified user.

18. The non-transitory computer-readable medium of claim 14, wherein each PCR curve with a confidence level at or above a predefined threshold is classified as true positive or true negative.

19. The system of claim 1, wherein the user interface depicts a graphical indication of false positive and/or a graphical indication of a false negative by highlighting a generated PCR curve with a graphical bounding box or a color.

20. The system of claim 19, wherein, true positive result and a true negative result without any highlighting of the graphical bounding box or the color.

* * * * *